Nov. 12, 1963 O. O. DUNHAM Plant Pat. 2,298
CHRYSANTHEMUM PLANT
Filed April 2, 1962
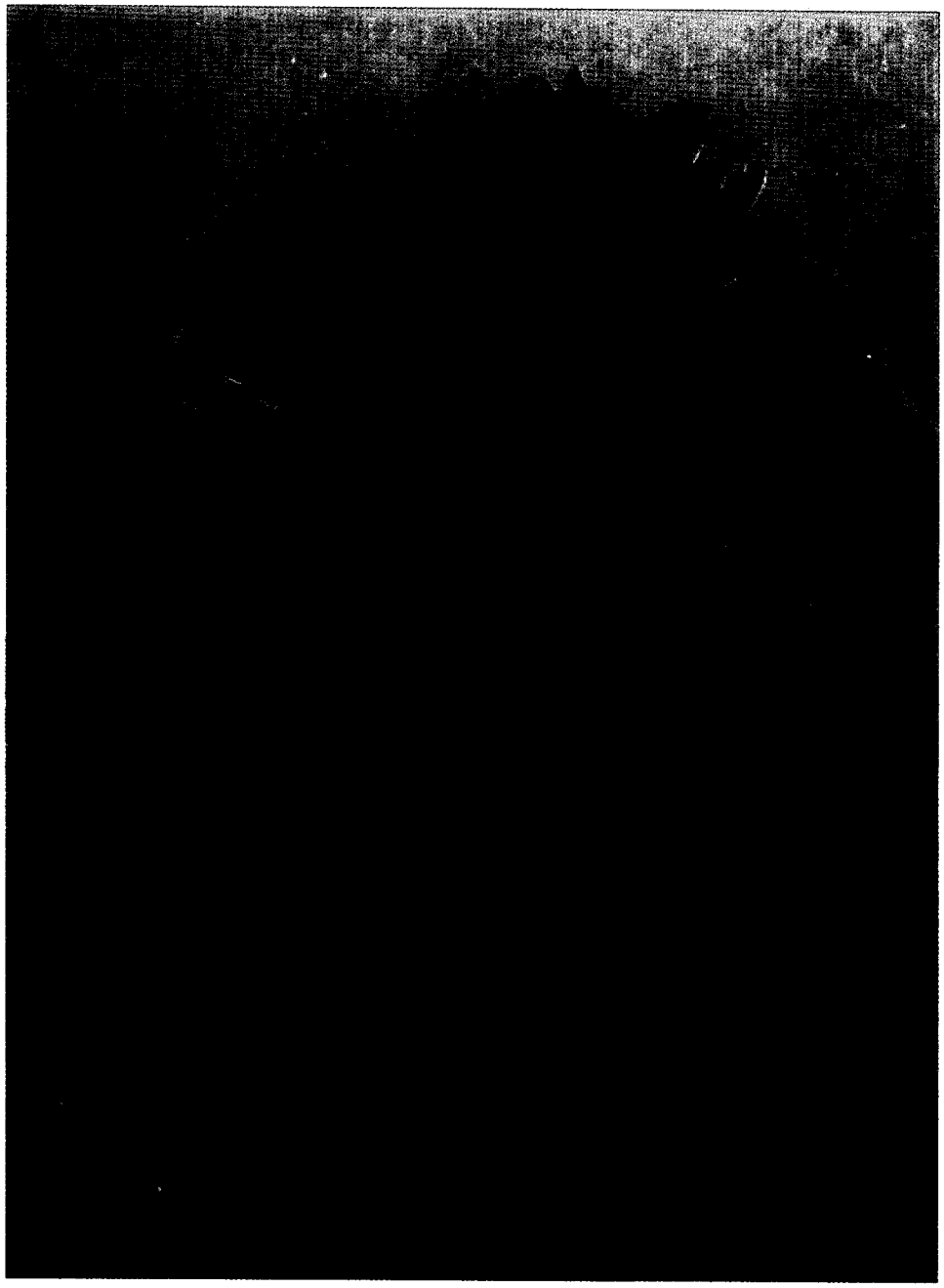
Inventor:
O. O. DUNHAM
by Robb & Robb
attorneys United States Patent Office Plant Pat. 2,298
Patented Nov. 12, 1963

2,298

CHRYSANTHEMUM PLANT

Orville O. Dunham, Rte. 4, Niles, Mich.

Filed Apr. 2, 1962, Ser. No. 184,615
1 Claim. (Cl. Plt.—82)

My present invention comprises a new and distinct variety of chrysanthemum plant, derived as a result of crossing the variety, "Lipstick," an unpatented variety of my own introduction, with another unpatented variety known as "Tokay."

The object of this invention is to produce a new and distinct variety of chrysanthemum of the indicum type having novel characteristics making the same different from the garden mums now in commerce, and particularly characterized by the intense color of the blooms, the outstanding habit and vigorous growth with attractive foliage derived from one of the parents, with long lastingness of the flower color a particular phase of improvement. The foliage habit and bloom are definite improvements over either of the parents.

My developments in the field of chrysanthemums are the result of study and conducting of intensive programs to derive the present new variety which is one of the results thereof, requiring careful selection and cross breeding of various plants from various parent plants to improve on the characteristics of the specific plants and the general strain of the so-called American garden mum, certain of the characteristics desirably being early flowering and continuous flowering thereafter.

In consequence of the specific hybridization previously referred to I have produced my present new and distinct variety of chrysanthemum characterized by the glowing dark red to moderate red color of its blooms, the long lastingness of said color, the improved habit, vigorous growth and abundant foliage together with the compact form of the plant in which the blooms are found on strong, short, stiff stems.

The blooms of my new variety are more specifically of a dark red to moderate red color (Nickerson Color Fan published by The Munsell Color Company), the overall impression of the blooms being of a very intense color which is rich and glowing. As grown in the vicinity of Niles, Michigan, in uniform culture, plants of my new variety grow to an average height of 12″ to 16″ and in compact form in most cases.

A number of the characteristics of my new variety are derived from both parents but the new variety includes better characteristics than either separately, primarily in the color of the blooms and in the abundant nature of the foliage, this differing from both of the parents and from other known varieties.

My new variety when grown in the region of Niles, Michigan, produces profuse blooms from late September, continuously until a killing frost, the blooms being found in clusters irregularly arranged, with short, strong stems on each plant.

My new variety has been asexually reproduced by cuttings in the vicinity of Niles, Michigan, and has been found to retain its distinctive characteristics through successive asexual reproduction.

The accompanying drawing forming a part hereof shows a typical plant of my new variety of chrysanthemum.

The following is a detailed description of my new variety of chrysanthemum plant, the color references being to the Nickerson Color Fan published by The Munsell Color Company:

*Description*

Parentage: Seedling.
- *Seed parent.*—"Lipstick" (unpatented).
- *Pollen parent.*—"Tokay" (unpatented).

Classification: Botanic—*Chrysanthemum indicum.*

*Flower*

Blooming habit: Blooms continuously from late September until a killing frost. Observations were made in the vicinity of Niles, Michigan, during September and October.

Bud:
- *Size.*—Small.
- *Form.*—Short with flat top.
- The bud is not affected by hot or wet weather.

Color:
- *When petals begin to unfurl.*—2.5R 3/7.
- *When half blown.*—Inside of petals—5R 3/7. Reverse of petals—5R 3/7.
- *Calyx.*—Shape—funnel. Size—small. Aspect—hairy.
- *Peduncle.* — Length — medium. Aspect — rough. Strength—stiff and erect. Bud opens well and is not affected by adverse weather conditions.

Bloom:
- *Size.*—Small. Average size when fully expanded—1½″–2″.
- *Borne.*—In clusters and irregular.
- *Stems.*—Short, strong.
- *Form.*—When first open—flat. Permanence—retains its form to the end.
- *Petalage.*—Very double, many petals and stamens hidden. Innumerable petals under normal conditions.
- *Color.*—Center of flower—2.5R 3/7. Outer petals—2.5R 4/10. Base of petals—(singlet)—2.5R 3/7. Inside of petals—2.5R 4/10. Reverse of petals—2.5R 4/10. General tonality from a distance—rich deep red between 2.5R 4/10 and 2.5R 3/7.
- *Discoloration.*—General tonality at end of: First day—retains same color. Second day—retains much the same color. Third day—lightens slightly.

Petals:
- *Texture.*—Thin; not materially affected by hot or wet weather.
- *Appearance.*—Inside—velvety. Outside—satiny.
- *Form.*—Oval.
- *Arrangement.*—Imbricated.
- *Persistence.*—Hang on and dry.
- *Fragrance.*—None.

Genital organs:
- *Stamens, anthers.*—Small, few.
- *Arrangement.*—Regular around styles.
- *Stamens, filaments.*—Medium length.
- *Styles.*—Columnar and short.
- *Ovaries.*—All enclosed in calyx.

Plant:

*Form.*—Bush.

*Growth.*—Vigorous, dwarf and branching.

Foliage:

*Size.*—Medium.

*Quantity.*—Abundant.

*Shape.*—3 lobed.

*Texture.*—Upper side—smooth. Under side—smooth.

*Edge.*—Smooth.

*Stipules.*—Short.

I claim:

A new and distinct variety of chrysanthemum plant substantially as herein disclosed, characterized as to novelty by the glowing dark red to moderate red color of its blooms, the tendency to retain said color for a long period of time, the improved habit, vigorous growth, abundant foliage, the compact form of the plant, with strong, short stems, and continuous blooming until killing frost.

No references cited.